United States Patent [19]

Sasaki et al.

[11] 3,962,455
[45] June 8, 1976

[54] ANTIBIOTIC ASCOFURANONE AND PROCESS FOR THE PRODUCTION THEREOF

[75] Inventors: Hiroshi Sasaki; Tsuneo Okutomi; Tomoyoshi Hosokawa; Yoshiharu Nawata; Kunio Ando, all of Tokyo, Japan

[73] Assignee: Chugai Seiyaku Kabushiki Kaisha, Tokyo, Japan

[22] Filed: Nov. 22, 1974

[21] Appl. No.: 526,175

Related U.S. Application Data

[63] Continuation-in-part of Ser. No. 364,033, May 25, 1973, Pat. No. 3,873,529.

[52] U.S. Cl. .............................................. 424/285
[51] Int. Cl.² ......................................... A61K 31/35
[58] Field of Search .................................... 424/285

[56] References Cited
OTHER PUBLICATIONS
Chemical Abstracts 79: 91871e (1973).

*Primary Examiner*—Jerome D. Goldberg
*Attorney, Agent, or Firm*—Browdy and Neimark

[57] ABSTRACT

A novel antibiotic designated as ascofuranone having useful hypotensive and hypolipidemic activities produced from an ascofuranone-producing microorganism of *Ascochyta viciae* Libert by an aerobic culturing, and processes for the production and use of ascofuranone are disclosed.

8 Claims, 4 Drawing Figures

ANTIBIOTIC ASCOFURANONE AND PROCESS FOR THE PRODUCTION THEREOF

CROSS REFERENCE TO RELATED APPLICATION

The present application is a divisional in the form of a continuation-in-part of U.S. application Ser. No. 364,033 filed May 25, 1973, now U.S. Pat. No. 3,873,529.

BACKGROUND OF THE INVENTION

Field of the Invention

This invention relates to a novel antibiotic ascofuranone, and processes for its use. More particularly, this invention relates to a novel antibiotic ascofuranone having excellent hypotensive and hypolipidemic activities in mammals for use in the form of a therapeutic composition including ascofuranone to be applied to mammals including human beings, and a method for using such a composition.

Summary of the Invention

As a result of extensive screenings of various microorganisms in order to obtain new and useful antibiotics, it is found that a novel antibiotic is accumulated in the mycelium of *Ascochyta viciae* Libert, a phytopathogenic species which is classified into a fungus in the taxonomy when the microorganism is cultured aerobically in a culture medium.

The microorganism used in the present invention is a well known organism and deposited, as a culture collection, with the Agency of Industrial Science & Technology, Fermentation Research Institute, Japan, under deposit number FERM-P 129. The antibiotic of the present invention does not exhibit any appreciable antibacterial and antifungal activities but does show excellent hypotensive and hypolipidemic activities in mammals. This antibiotic was designated as "Ascofuranone" by the inventor of the present invention.

The microorganism, *Ascochyta viciae* Libert, does not form any spores and grows with thin aerial mycelium on a solid medium and with an abundant small aerial micelium in a liquid medium. The mycelia have a pink-red color.

An object of this invention is to provide a novel antibiotic designated as ascofuranone having excellent hypotensive and hypolipidemic activities.

Another object is to provide a hypotensive therapeutic composition to be applied to mammals including human beings comprising as an effective ingredient ascofuranone in an amount sufficient to exhibit a hypotensive activity and a pharaceutically acceptable carrier and a method for diminishing blood pressure in mammals by administering this composition.

Yet another object is to provide a hypolipidemic therapeutic composition to be applied to mammals including human beings comprising as an effective ingredient ascofuranone in an amount sufficient to exhibit a hypotensive activity and a pharmaceutically acceptable carrier.

Another object is to provide a method for reducing the serum lipid level of mammals by administering ascofuranone.

BRIEF DESCRIPTION OF THE ACCOMPANYING DRAWINGS

DETAILED DESCRIPTION OF THE INVENTION

Figure 1:
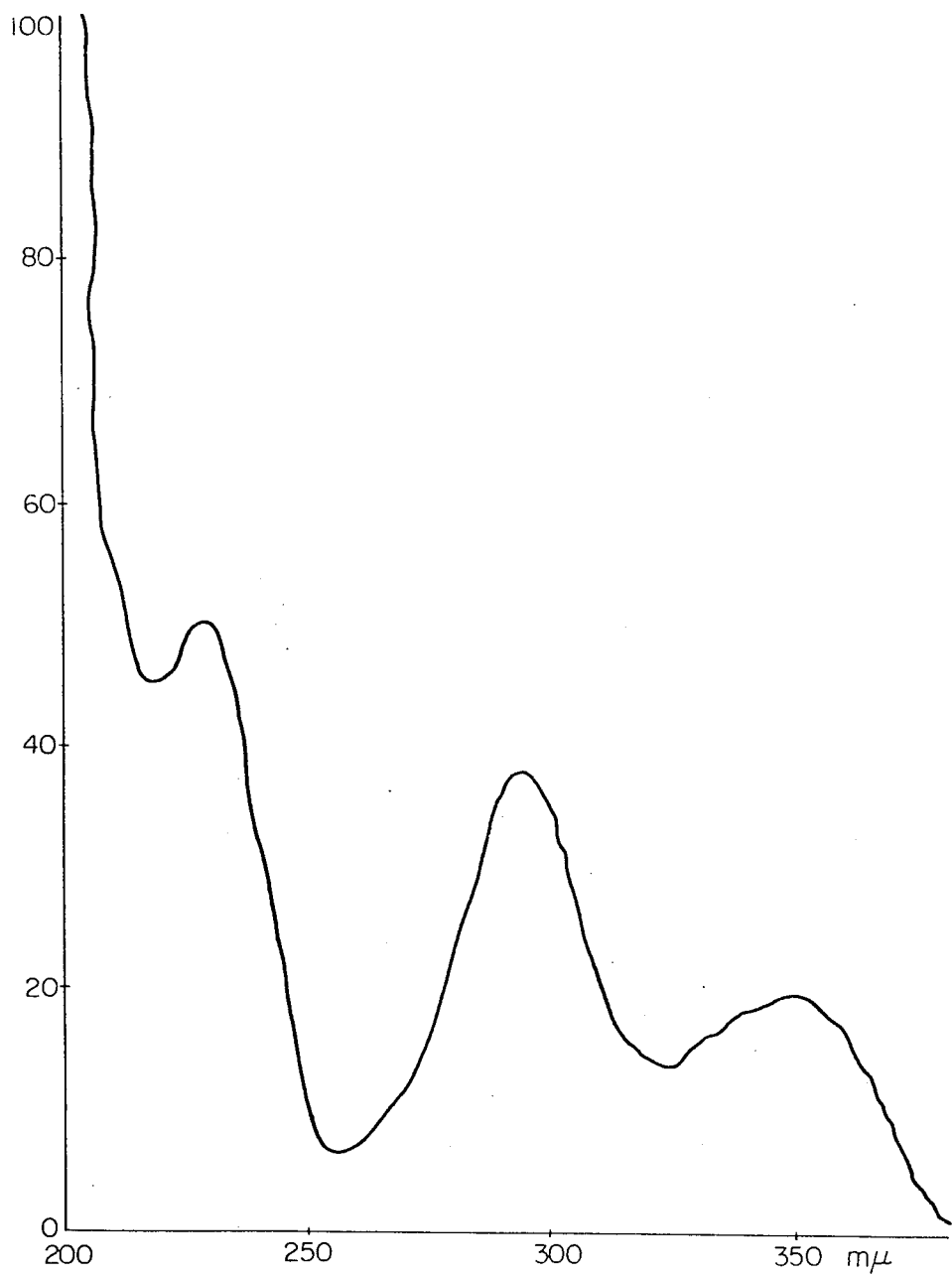
FIG. 1 is a graph showing an ultraviolet absorption spectrum of the antibiotic ascofuranone of the present invention.
Figure 2:
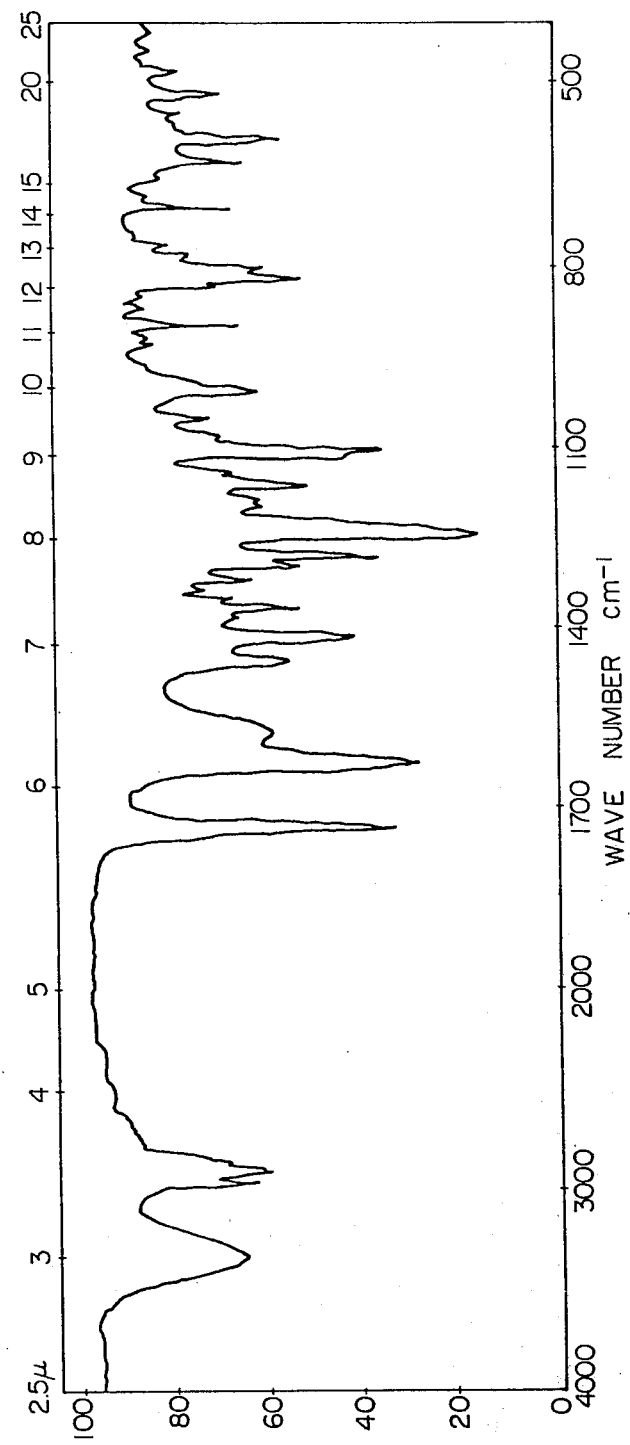
FIG. 2 is a graph showing an infrared absorption spectrum of the antibiotic ascofuranone of the present invention.

In producing ascofuranone in accordance with the process of this invention, an ascofuranone-producing microorganism of *Ascochyta viciae* Libert can be cultured in a chemically defined or natural culture medium containing carbon sources, nitrogen sources, inorganic salts or a small amount of nutrients at a temperature of from 25° to 30°C until a substantial amount of ascofuranone is accumulated in the mycelium of the culture, i.e., for a period of from 3 to 10 days while shaking or under submerged conditions and ascofuranone can then be isolated from the mycelium of the culture broth.

The isolation of ascofuranone from the mycelium obtained by cultivation and subsequent purification of the isolated ascofuranone can be carried out by the techniques well-known in the art. In a preferred embodiment, the isolation and purification can be effected by filtering the culture broth to separate the mycelium as a filter cake, adding a water-miscible organic solvent such as methanol, ethanol or acetone to extract ascofuranone from the mycelium, filtering the mixture to remove the mycelium, concentrating the extract to distil off the solvent, adjusting the pH of the residue to about 3, extracting the resulting mixture with ethyl acetate or hexane, concentrating the separated organic layer containing dissolved ascofuranone and purifying the organic layer by column chromatography to obtain ascofuranone having a high purity. The isolation of ascofuranone from the mycelium also may be carried out by one step by extracting the mycelium with the solvent system consisting of methanol and an alkane series hydrocarbon solvent having one or more of chlorine atom as a substituent, for example chloroform, 1,1,1-trichloroethane or dichloromethane.

The ascofuranone thus obtained is a fat-soluble substance having a molecular weight of 420 and the empirical formula $C_{23}H_{29}O_5Cl$. The structural formula of the compound is as follows:

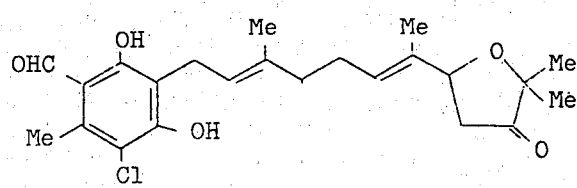

Ascofuranone is a white needle crystalline substance having a melting point at 84°C. It is not soluble in water, but is easily soluble in ethyl acetate, benzene, chloroform and acetone and is soluble in methanol, ethanol and hexane. The ultraviolet absorption spectrum exhibits three absorption maxima at $\lambda_{max}^{EtOH}$ 228 mn ($\epsilon$ = 20300), $\lambda_{max}^{EtOH}$ 295 mn ($\epsilon$ = 15000) and $\lambda_{max}^{EtOH}$ 350 mn ($\epsilon$ = 8200) as determined in ethanol. The infrared absorption spectrum exhibits the presence of an OH group, a CH group and a > CO group with characteristic absorptions at 3320 cm$^{-1}$; 2970 – 2860 cm$^{-1}$; 1735 cm$^{-1}$ and 1635 cm$^{-1}$, respectively. Ascofuranone shows positive Beilstein and ferric chloride reactions. The elementary analysis calculated for $C_{23}H_{29}O_5Cl$ is C, 65.62%; H, 6.94%; Cl, 8.43%; and found C, 65.24%; H, 6.93%; and Cl, 8.26%. The R$_f$ value in thin layer chromatography was 0.42 (silica gel) by the solvent system of petroleum ether: acetone (3:1).

Among the important utilities for the ascofuranone of the present invention and for compositions containing ascofuranone as the active principle are the hypolipidemic and hypotensive activities thereof. The amount of ascofuranone to be present in compositions for these two utilities differs according to the kind of animals to which it is to be administered and the form of its preparation. However, we have found that if ascofuranone is orally administered daily in an amount of 0.05 mg/kg. body weight or more it comes to exhibit its desired activity after several consecutive days, so it may be administered usually in an amount of 0.05–500 mg/kg. body weight a day, and preferably in an amount of 0.5–50 mg/kg. body weight a day. It should also be understood that in the present invention ascofuranone may be used in combination with other hypotensive agents such as reserpine and dipyridamol or, when used for its hypolipidemic activity, it may be used in conjunction with other known hypolipidemic agents.

The composition, however, may be administered to hypertensive mammals in any amount effective to exert a hypotensive activity and it may be administered to hyperlipidemic mammals in any amount effective to exert a hypolipidemic activity.

Ascofuranone is a substance which is scarcely-soluble in water; not only can it be formed into a tablet, a granule with conventional pharmaceutical acceptable carriers such as lactose, starch, crystalline cellulose, kaolin, calcium carbonate and talc, which are ordinarily used in medicines, but also it can be optionally formed into a capsule by encapsulating said granule and powder. It can also be formed into a suspension in a conventional pharmaceutically acceptable liquid carrier such as aqueous gum arabic solution and aqueous sucrose solution.

In order to reduce the high blood pressure of mammals with the present pharmaceutical composition that is prepared by the aforementioned process, said composition shall be orally administered to mammals once or several times a day. Particularly for a human being, it is desirable to administer it three times a day, for example, after every meal of the day; for animals other than men, the composition may be applied either independently or in combination with fodder. As mentioned before, the amount of the composition to be administered to mammals depends upon to which animal or in what form of preparation it is administered, but in the usual case, it is our intention to use 0.05–500 mg/kg. body weight a day of the effective substance, i.e. ascofuranone, and preferably 0.5–50 mg/kg. body weight a day. Though enough experiments have not yet been carried out to determine the appropriate dose of ascofuranone for human beings in all cases, it can be said that a tablet containing 50 mg of ascofuranone shows a good result when it is taken after every meal of the day.

For the purpose of lowering high blood pressure or lowering the serum lipid content of the blood the present pharmaceutical composition can be administered to all mammals such as human beings, monkeys, bovines, dogs, cats, pigs and so on.

The present invention is further illustrated by the following Experiments and Examples, but they are not to be construed as limiting the scope of this invention.

EXAMPLE 1

70 l of a culture medium comprising 5% glucose, 0.5% peptone, 0.2% yeast extract, 0.1% ammonium chloride, 0.06% potassium dihydrogen phosphate, 0.04% magnesium sulfate and 1.0% calcium carbonate was inoculated with 0.45 l of a seed culture of *Ascochyta viciae* Libert and the inoculated microorganism was cultured at a temperature of 27°C for a period of 96 hours while aerating at a rate of 30 l/minute and stirring at 150 rpm. After completion of cultivation, 15 l of methanol was added to the mycelium obtained by filtration of the culture broth, and the mixture was allowed to extract overnight at room temperature. The mycelium was then removed by filtration, and the filtrate was concentrated under reduced pressure to remove methanol. The resulting concentrate was adjusted to a pH of 3.0 with dilute hydrochloric acid. The concentrate was then extracted twice with 3 l of ethyl acetate, and the extract was concentrated under reduced pressure to remove ethyl acetate. The oily substance thus obtained was developed in a silica gel column packed with benzene, and the column was eluted with a solvent system consisting of benzene-methanol (97:3). Fractions in the eluate which were found to have an antiviral activity were collected and concentrated under reduced pressure to obtain 5 g of ascofuranone as needle crystals.

EXAMPLE 2

70 l of a culture medium comprising 3.0% glucose, 1.0% glycerin, 0.5% peptone, 0.2% corn steep liquor, 0.1% ammonium chloride, 0.06% potassium dihydrogen phosphate, 0.04% magnesium sulfate and 1.0% calcium carbonate was inoculated with 0.35 l of a seed culture of *Ascochyta viciae* Libert and the inoculated microorganism was cultured at a temperature of 27°C for a period of 96 hours while aerating at a rate of 60 l/minute and stirring at 200 rpm. After completion of cultivation, 10 l of acetone was added to the nycelium obtained by filtration of the culture broth, and the mixture was allowed to extract overnight at room temperature. The mycelium was then removed by filtration, and the filtrate was concentrated under reduced pressure. The resulting concentrate was adjusted to a pH of 3.0 with dilute hydrochloric acid. The concentrate was then extracted twice with 3 l of hexane, and the extract was dried over sodium sulfate. After separation of sodium sulfate by filtration, the filtrate was concentrated under reduced pressure to obtain crystals of ascofuranone. The mother liquor was concentrated, and, after addition of petroleum ether, the mixture was allowed to stand at a temperature of −10°C to obtain 3 g of ascofuranone as white needle crystals.

The elementary analysis, infrared absorption spectrum and ultraviolet absorption spectrum of the product were consistent with those of the product obtained in Example 1.

EXAMPLE 3

Examples of suitable compositions containing the ascofuranone of the present invention are the following:

a. Capsule

To 100 g of pulverized ascofuranone were added 358 g of lactose and 2 g of magnesium stearate and they were mixed completely. The mixture was then stuffed into hard gelatin capsules each weighing 65 mg; one capsule was filled with 230 mg of the mixture.

b. Powder

To 50 g of pulverized ascofuranone were added 404 g of lactose, 45 g of microcrystalline cellulose and 1 g of magnesium stearate and they were mixed completely. The mixture was then ground into powder.

c. Tablet - I

To 100 g of pulverized ascofuranone were added 210 g of lactose, 72 g of microcrystalline cellulose, 14 g of corn starch and 4 g of magnesium stearate and they were thoroughly mixed. Then, with a tablet machine, the mixture was formed into tablets each tablet being 8 mm in diameter and 200 mm in weight.

d. Tablet - II

After being passed through a screen of 50 mesh (Tyler), 100 g of pulverized ascofuranone was mixed with 273 g of lactose and 20 g of calcium carboxymethyl cellulose, and the mixture was then kneaded with a starch paste made of 4 g of corn starch and water. The resulting mixture was granulated by a granulating machine and dried and the granules were passed through a screen of 14 mesh (Tyler). After addition of and mixing with 3 g of magnesium stearate, the mixture was formed into tablets, each being 8 mm in diameter and 20 mg in weight.

EXPERIMENT 1

Antimicrobial Activity

The antimicrobial activities of ascofuranone against various bacteria, yeasts and fungi in an aqueous solution of ascofuranone at a concentration of 100 μg/ml were determined by the agar streak method. The results obtained are shown in Table 1 below:

Table 1

Antimicrobial Activity of Ascofuranone by the Agar Streak Method (in 100 μg/ml Solution)

| Test Ortanism | Growth Inhibitory | Time Observed (hr.) |
|---|---|---|
| Bacillus subtilis | — | 20 |
| Staphylococcus aureus | — | 20 |
| Sarcina lutea | — | 20 |
| Escherichia coli | — | 20 |
| Shigella flexneri | — | 20 |
| Xanthomonas oryzae | — | 20 |
| Candida albicans | — | 20 |
| Saccharomyces cerevisiae | — | 20 |
| Aspergillus oryzae | — | 48 |
| Rhizopus oryzae | — | 48 |

As is apparent from the results shown in Table 1, ascofuranone does not show any appreciable antimicrobial activities against bacteria, yeasts and fungi.

EXPERIMENT 2

Hypolipidemic Activity

The hypolipidemic activity of ascofuranone in the rat serum was determined under various conditions. The quantitative determination of each of the lipids in the serum was conducted in accordance with the following methods: Total choresterol was determined by a modified method of Zurkowski (Clinical Chemistry, 10, 451, 1964), triglycerides were determined by the Van Handel method (J. Lab. & Clin. Med., 50, 152, 1957), phospholipids were determined by the Zilversmit-Yoshida method (J. Lab. & Clin. Med., 35, 155, 1950 and Clinical Pathology 10, 194, 1962) and free fatty acids were determined by the Itaya-Ui method (J. Lipid Res., 6, 16, 1965).

1. To a group of five Wister-male rats, each weighing about 185 g, was administered orally ascofuranone at a dose level of 20 mg/head, and, 6 hours after administration, a serum lipid level in each of the rats was determined by the method described above. The results obtained are shown in Table 2 below in comparison with the results obtained in a control rat group (no medication).

Table 2

| Lipids | Control Group | Administration Group | % Reduction |
|---|---|---|---|
| Total Cholesterol | 66 mg/dl | 54 mg/dl | 18% |
| Triglyceride | 60 mg/dl | 39 mg/dl | 35% |
| Phospholipid | 105 mg/dl | 92 mg/dl | 12% |
| Free Fatty Acid | 51 μeq./dl | 44 μeq./dl | 14% |

2. A group of five Wister-male rats, each weighing about 270 g, was fed a usual solid feed (Trade Name, CLEA CE-2 available from Japan Clea Co., Ltd. ) and, during which time ascofuranone was administered in a dose level of 20 mg/head/day for consecutive 10 days. At the end of this period, a serum lipid level in each of the rats was determined by the method described above. The results obtained are shown in Table 3 below in comparison with the results obtained in a control group which received 2% aqueous gum arabic.

Table 3

| Lipids | Control Group | Administration Group | % Reduction |
|---|---|---|---|
| Total Cholesterol | 68 mg/dl | 56 mg/dl | 18% |
| Triglyceride | 44 mg/dl | 22 mg/dl | 50% |
| Phospholipid | 157 mg/dl | 104 mg/dl | 34% |
| Free Fatty Acid | 91 μeq/dl | 73 μeq/dl | 20% |

3. A group of five Wister-male rats, each weighing about 265 g, was fed a high-fat feed (10 g of cholesterol; 95 g of hydrogenated coconut oil, 2 g of cholic acid, 150 g of casein and 670 g of sucrose having added to 1 Kg of a usual solid feed) and during which time ascofuranone was administered in the same manner as described in (2) above. The results obtained are shown in Table 4 below:

Table 4

| Lipids | Control Group | Administration Group | % Reduction |
|---|---|---|---|
| Total Cholesterol | 97 mg/dl | 69 mg/dl | 29% |
| Triglyceride | 72 mg/dl | 40 mg/dl | 44% |
| Phospholipid | 214 mg/dl | 163 mg/dl | 24% |
| Free Fatty Acid | 82 µeq/dl | 70 µeq/dl | 15% |

EXPERIMENT 3

Hypotensive Activity

1. After 30 mg/kg. body weight of sodium 5-ethyl-5-(1-methylbutyl)-barbiturate was intraperitoneally administered to a Wister strain male rat weighing about 300 g, different amounts of ascofuranone (5 mg/kg, 10 mg/kg and 20 mg/kg body weight, respectively) were administered to the same rat as a suspension in a 2% aqueous gum arabic solution. The carotid arterial pressure of the rat thus treated was measured every ten minutes by an RP-3 model transducer (manufactured by Nihon Koden-sha). The results of this measurement are shown below:

Hypotensive Activity of Ascofuranone

|  | Initial | 30 min | 60 min | 120 min | 240 min | 360 min |
|---|---|---|---|---|---|---|
| 4% gum arabic | 180+9 | 183±7 | 182+8 | 178+7 | 182+8 | 182+8 |
| 10 mg/kg of ascofuranone | 182+8 | 178+6 | 170±4 | 162+6 | 171+6 | 173+7 |
| 4% gum arabic | 180+8 | 177+8 | 178+8 ** | 180+7 * | 175+8 | 178+8 |
| 30 mg/kg of ascofuranone | 185+9 | 177+7 | 150+5 | 157±7 | 175+6 | 180+9 |

Each group consisted of 6 rats.
Numerical figures are all expressed in terms of mm Hg as a combination of average value and standard error.

* P<0.05
** P<0.01

| Dose of Ascofuranone | | Initial | Carotid Arterial Pressure (mm Hg) | | | | |
|---|---|---|---|---|---|---|---|
| | | | 10 min | 20 min | 30 min | 40 min | 50 min |
| 5 mg/kg | systolic | 144 | — | — | 135 | 137 | 149 |
| | diastolic | 113 | — | — | 111 | 108 | 120 |
| | mean | 138 | — | — | 127 | 123 | 141 |
| 10 mg/kg | systolic | 156 | — | — | 155 | 113 | 106 |
| | diastolic | 113 | — | — | 118 | 71 | 64 |
| | mean | 125 | — | — | 129 | 80 | 77 |
| 20 mg/kg | systolic | 207 | 188 | 142 | 134 | 142 | 120 |
| | diastolic | 141 | 136 | 108 | 102 | 107 | 82 |
| | mean | 157 | 147 | 121 | 106 | 115 | 88 |

2. Twenty-four spontaneous hypertensive rats each weighing about 210 g were divided into four groups. Two of the groups remained controls and the others were treated with the composition of the present invention.

Suspended in a 4% aqueous gum arabic solution, ascofuranone was orally administered in a dose of 10 mg and 30 mg per kg of the weight of each rat of the test groups. The control groups were only treated with 4% aqueous gum arabic solution.

The tail arterial pressure of all the rats was measured by a plethysmographic tail method ½, 1, 2, 4 and 6 hours after administration of ascofuranone.

It was observed that the blood pressure of rats which were given 10 mg/kg of ascofuranone and of those given 30 mg/kg of ascofuranone dropped within 1 hour after administration. Compared with the control groups, those which were treated with 30 mg/kg of ascofuranone showed a statistically significant drop in blood pressure after 1 hour and 2 hours, respectively.

It will be obvious to those skilled in the art that various changes may be made without departing from the scope of the invention and the invention is not to be considered limited to what is shown in the drawing and described in the specification.

What is claimed is:

1. A therapeutic composition having hypotensive activity comprising an effective amount to create a hypotensive effect of ascofuranone, of the formula:

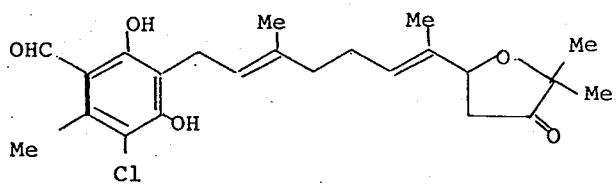

in a pharmaceutically acceptable carrier.

2. A composition in accordance with claim 1 further including reserpine or dipyridamol.

3. A composition in accordance with claim 1, wherein said composition is prepared in the form of a tablet, a granule, a powder or a capsule.

4. A method for diminishing blood pressure in mammals comprising administering to a hypertensive mammal an effective amount of the composition of claim 1 to exert a hypotensive activity.

5. A method in accordance with claim 4 wherein said composition is administered in a dosage of 0.05–500 mg/kg body weight per day.

6. A method in accordance with claim 5 wherein said dosage is 0.5–50 mg/kg body weight per day.

7. A method in accordance with claim 4, wherein said hypertensive mammal is a hypertensive human being.

8. A method in accordance with claim 4, wherein said hypertensive mammal is a hypertensive monkey, bovine, dog, cat or pig.

* * * * *

UNITED STATES PATENT AND TRADEMARK OFFICE
CERTIFICATE OF CORRECTION

PATENT NO. : 3,962,455
DATED : June 8, 1976
INVENTOR(S) : SASAKI et al.

Figure 3:
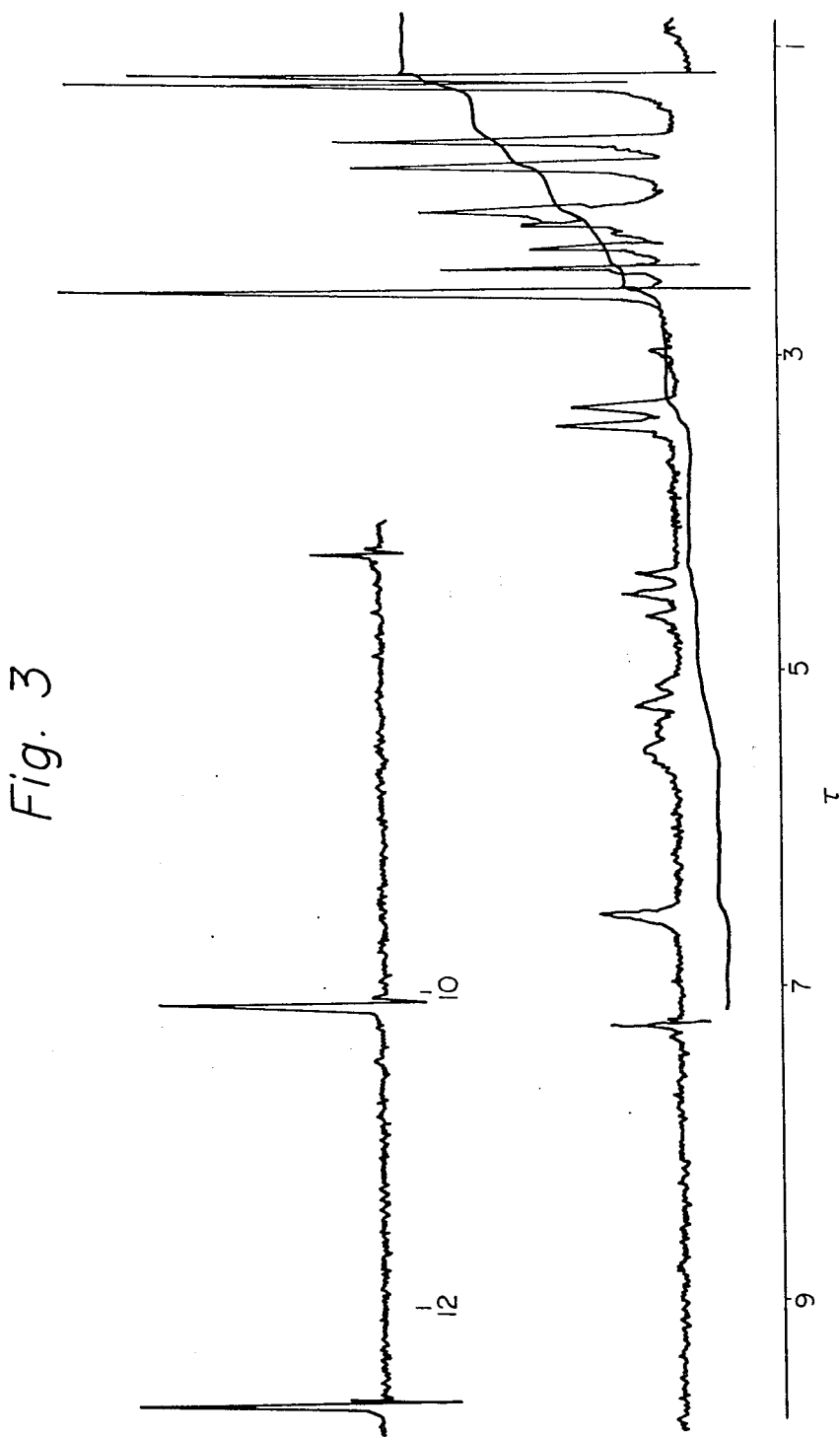
FIG. 3 is a graph showing a nuclear magnetic resonance spectrum of the antibiotic ascofuranone of the present invention.
Figure 4:
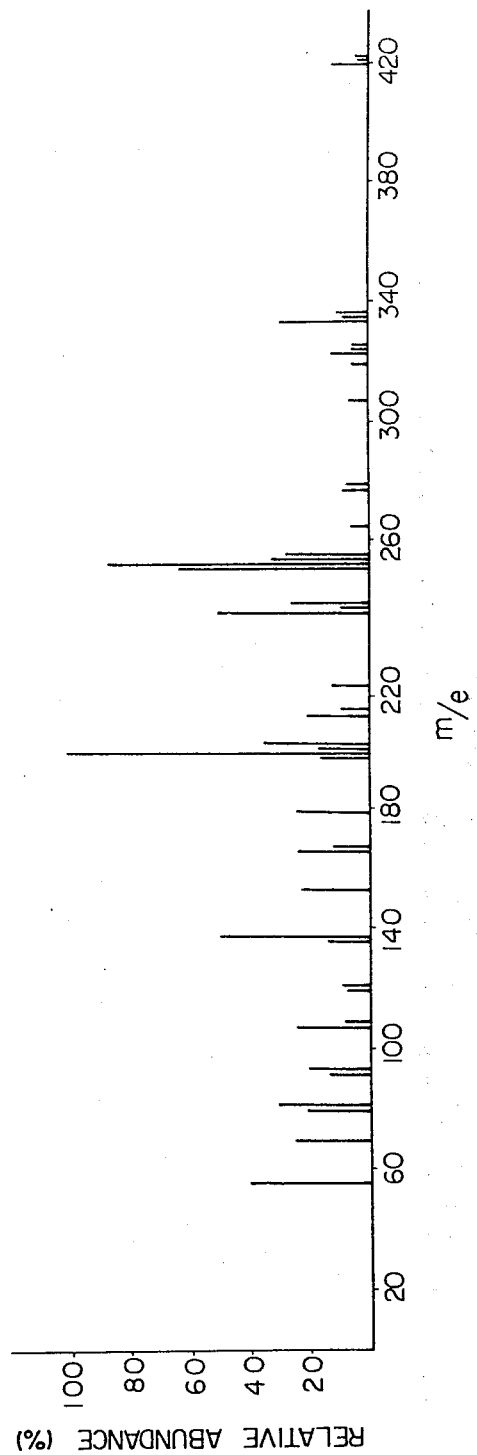
FIG. 4 is a graph showing a mass spectrum of the antibiotic ascofuranone of the present invention.

It is certified that error appears in the above-identified patent and that said Letters Patent are hereby corrected as shown below:

In the drawing Fig. 3, the unit "τ" should read --ppm (δ)--

In the Table following line 13 in Column 8, change "+"(every occurrence in the Table) to read --$\pm$--

Signed and Sealed this

Tenth Day of January 1978

[SEAL]

Attest:

RUTH C. MASON
*Attesting Officer*

LUTRELLE F. PARKER
*Acting Commissioner of Patents and Trademarks*